United States Patent [19]

Kerb et al.

[11] 4,045,574
[45] Aug. 30, 1977

[54] D-HOMO-20-KETOPREGNANES

[75] Inventors: Ulrich Kerb; Rudolf Wiechert; Klaus Kieslich; Karl Petzoldt; Helmut Wachtel; Dieter Palenschat; Reinhard Horowski; Gert Paschelke; Wolfgang Kehr, all of Berlin, Germany

[73] Assignee: Schering Aktiengesellschaft, Berlin & Bergkamen, Germany

[21] Appl. No.: 528,328

[22] Filed: Nov. 29, 1974

[30] Foreign Application Priority Data

Nov. 30, 1973 Germany .......................... 2360443
Sept. 19, 1974 Germany .......................... 2445161

[51] Int. Cl.² .................. A01N 9/14; A61K 31/255; C07C 49/26
[52] U.S. Cl. .................. 424/303; 260/400; 260/405; 260/456 R; 260/456 P; 260/473 A; 260/476 C; 260/483; 260/586 E; 424/308; 424/311; 424/312; 424/313; 424/331
[58] Field of Search .......... 260/586 E, 456 R, 488 B, 260/473 A, 476 C, 483, 400, 405; 424/331, 308, 311, 303, 312, 313, 314

[56] References Cited

U.S. PATENT DOCUMENTS

| | | | |
|---|---|---|---|
| 2,860,158 | 11/1958 | Clinton | 260/488 B |
| 3,686,223 | 8/1972 | Miller | 260/586 E |
| 3,833,621 | 9/1974 | Grunwell et al. | 260/397.4 |

*Primary Examiner*—Gerald A. Schwartz
*Attorney, Agent, or Firm*—Millen & White

[57] ABSTRACT

D-homo-20-ketopregnanes of the formula

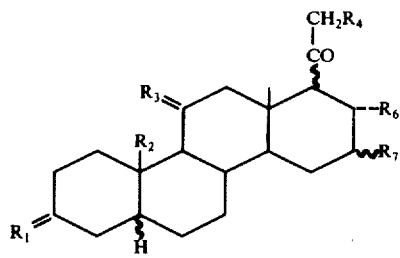

wherein $R_1$ is oxygen,

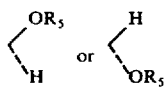

in which $R_5$ is hydrogen or lower acyl; $R_2$ is hydrogen or methyl; $R_3$ is oxygen,

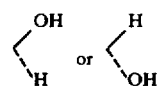

or two hydrogen atoms; $R_4$ is hydrogen, hydroxy or acyloxy; $R_6$ is hydrogen or methyl; and $R_7$ is hydrogen, acetyl, hydroxy or lower acyloxy in the α- or β-position possess CNS-depressant activity, including anesthesia upon parenteral administration, and are produced by hydrogenating the corresponding steroids having double bonded $C_5$ and/or $C_{16}$ carbon atoms.

23 Claims, No Drawings

D-HOMO-20-KETOPREGNANES

BACKGROUND OF THE INVENTION

This invention relates to novel D-homo-20-ketopregnanes having CNS-depressant activity.

It is known that several steroid compounds, especially those of the pregnane series, have a central nervous system depressant, anesthetic-narcotic activity and exert an influence on the membrane permeability [J. A. Sutton, Postgrad. Med. J., 48 Suppl. 2 (1972)].

SUMMARY OF THE INVENTION

In a composition aspect, this invention relates to novel D-homo-20-ketopregnanes of the general Formula I

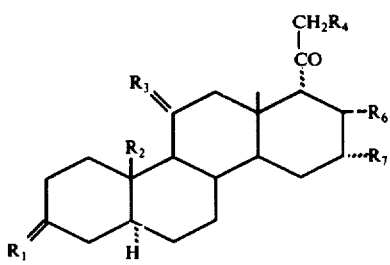

wherein $R_1$ is oxygen,

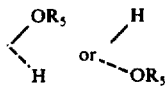

in which $R_5$ is hydrogen or lower acyl; $R_2$ is hydrogen or methyl; $R_3$ is oxygen,

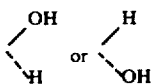

or two hydrogen atoms; $R_4$ is hydrogen, hydroxy or acyloxy; $R_6$ is hydrogen or methyl; and $R_7$ is hydrogen, acetyl, hydroxy or lower acyloxy in the α- or β-position.

In another composition aspect, this invention relates to pharmaceutical compositions comprising one or more compounds of this invention.

In process aspects, this invention relates to processes for the production of compounds of this invention and to their use for inducing CNS-depressant effects, especially general anesthesia.

DETAILED DISCUSSION

The wavy lines at the $C_5$ and $C_{17a}$ positions of Formula I mean the side chain at the C-17a carbon atom and the hydrogen atom in the 5-position can be in either the α- or β-position.

The term acyl means the acyl radical of an acid customarily employed for esterification reactions in the steroid chemistry. Preferred acids are hydrocarbon carboxylic acids of 1 to 15 carbon atoms. These carboxylic acids can be saturated or unsaturated, straight or branched chain, aliphatic, cycloaliphatic or aromatic. Contemplated equivalents thereof are the corresponding polybasic acids and acids substituted in the usual manner, for example by hydroxy, amino or oxo groups, or by halogen atoms, and other cycloaliphatic, aromatic, mixed aromatic-aliphatic and heterocyclic acids, which can also be substituted in the usual manner, e.g., by halogen atoms. Other contemplated equivalents are sulfuric acid, phosphoric acid and lower-alkyl sulfonic and arylsulfonic acids.

Examples of suitable acids for the formation of such acyl groups are acetic acids, propionic acid, caproic acid, enanthic acid, undecylic acid, oleic acid, trimethylacetic acid, haloacetic acids, e.g., dichloroacetic acid, cyclopentylpropionic acid, cyclohexylacetic acid, phenylpropionic acid, phenylacetic acid, phenoxyacetic acid, dialkylaminoacetic acids, piperidinoacetic acid, succinic acid and benzoic acid. Suitable for the production of water-soluble preparations are the monoesters of dibasic acids and the salts thereof, e.g., the hemisuccinate sodium salt.

Lower acyl means the acyl radical of a carboxylic or sulfonic acid of up to 8, preferably of up to 5 carbon atoms, e.g., alkanoic, including formic acid, acetic acid, propionic acid, butyric acid and caproic acid, and alkanesulfonic, e.g., methanesulfonic acid and ethanesulfonic acid.

Examples of classes of compounds within the scope of Claim 1 are those wherein a. $R_2$ is $CH_3$;
b. the side chain at the $C_{17a}$ carbon atoms is in the beta position, especially those of (a);
c. $R_6$ is H, especially those of (a) and (b);
d. $R_7$ is H, especially those of (a), (b) and (c);
e. the 5-position hydrogen atom is in the alpha position, especially those of (a), (b), (c) and (d);
f. $R_6$ is methyl and $R_7$ is H, especially those of (a), (b) and (e);
g. $R_6$ is H and $R_7$ is hydroxy or lower-alkanoyloxy, especially those of (a), (b) and (e).

In addition to the compounds of the examples hereinafter, other specific embodiments of this invention include:

3α-hydroxy-D-homo-19-nor-5α-pregnan-20-one,
3α-hydroxy-17β-methyl-D-homo-5α-pregnan-2o-one,
3α-acetoxy-17β-methyl-D-homo-5α-pregnan-20-one and 3α-acetoxy-D-homo-19-nor-5α-pregnan-20-one.

The novel D-homo-20-ketopregnanes possess valuable pharmacological properties. They are particularly effective for central-depressive, anesthetic-narcotic uses. They have a short induction period with a high effectiveness. Upon parenteral administration, these compounds, after a brief induction induce general anesthesia.

Compared to the known steroids of the pregnane series, the novel D-homo-20-ketopregnanes exhibit a surprisingly short induction period with concomitant high effectiveness. Thus, for example, 3α-hydroxy-D-homo-5α-pregnan-20-one is five times as effective, after one minute p.i. (after injection), as sodium 21-hydroxy-5β-pregnane-3,20-dione-21-hemisuccinate.

This superior anesthetic effectiveness was determined in male NMRI mice weighing 20–25 g. For this purpose, the steroid test compound was suspended in 10% polyhydroxyethylated castor oil and administered intravenously in a randomized arrangement in admixture with 0.9% NaCl solution. The injection volume was 10 ml./kg. of body weight and was injected within 10 seconds. Directly after the injection, the test animals were placed in supine position on a heated plate (35° C.) and the loss of the righting relex was determined. A loss of righting reflex was present if the test animals did not right themselves within 30 seconds into the prone position with all four paws in contact with the ground. Evaluation was accomplished by statistical probit analysis.

The compounds of this invention are especially suitable for the induction of narcosis, wherein the anesthesia is maintained after induction of narcosis by an inhalation anesthetic, such as, for example, ether, halothane, laughing gas, etc. For various therapeutic or diagnostic operations, the anesthetic effect of the compounds of this invention is also sufficient by itself. The anesthetic effect can be maintained in this case by repeated or continuous administration. The compounds of this invention generally lead to especially minor undesired side effects as compared to heretofore known steroidal anesthetics.

Anesthetics based on the compounds of this invention are formulated, in correspondence with the customary pharmaceutical practice, with the aid of one or more vehicles, solubilizers or binders. The preparations of the anesthetic compounds of this invention are generally administered intravenously, and in certain cases also by intramuscular injection, e.g., in children.

The range of application encompasses the use as an anesthetic, in the human as well as veterinary medicine. A dosage of 0.1-5 mg./kg. of body weight is generally sufficient for an average person upon intravenous administration. The preferred dosage range is from 0.2 to 2 mg./kg. The dose is dependent on the physical condition of the patient and the degree and duration of the desired narcotizing effect. By varying the dosage, it is possible to obtain durations of narcosis of 10 minutes up to 1 hour or more. If a longer narcosis period is to be maintained, the dosages can be repeated, wherein such repeated dosages generally correspond to the first dose or are lower doses. However, it is also possible to effect a continuous administration, for example in an amount of 0.05-1 mg./kg. per minute.

If the anesthetic preparations are to be administered intramuscularly, higher dosages are generally required, usually at least twice as high as those during intravenous application.

In a process aspect, this invention relates to a process for the preparation of D-homo-20-ketopregnanes of general Formula I, characterized in that the carbon-to-carbon double bonds of a D-homo-20-ketopregnane of general Formula II

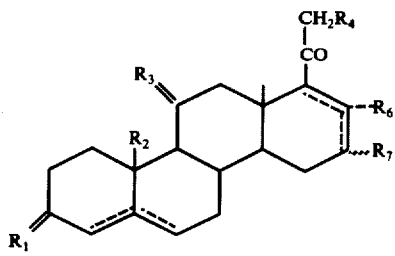

II wherein $R_1$, $R_2$, $R_3$, $R_4$, $R_5$, $R_6$ and $R_7$ have the values given above; $C_4=C_5=C_6$ and $C_{16}=C_{17}=C_{17a}$ represent single or double carbon-to-carbon bonds, but no cumulative double bonds, at least one being a double bond, are catalytically hydrogenated, and optionally concurrently or successively hydroxy groups are inverted or oxidized, keto groups are reduced, and/or any acyl groups present are hydrolyzed in a conventional manner and esterified with the finally desired acid.

The hydrogenation of a $\Delta^4$-, $\Delta^5$-, $\Delta^{16}$- and/or $\Delta^{17}$-double bonds is accomplished with hydrogen in the presence of a noble metal catalyst in finely divided form, such as, for example, palladium on a support material such as carbon, calcium carbonate, or strontium carbonate, or platinum black in an inert solvent, such as, for example, methanol, ethanol, tetrahydrofuran, dimethylformamide, dimethylacetamide, dioxane, ethyl acetate, or a mixture of these solvents.

To oxidize hydroxy groups in the 3- or 11-position, the D-homo steroid is taken up in a suitable solvent and then treated with chromic acid in a suitable reaction medium, e.g., glacial acetic acid or sulfuric acid/acetone or pyridine/methylene chloride, or with pyridine-sulfur trioxide complex in dimethyl sulfoxide/trietylamine.

For the selective oxidation of the 3-hydroxy group in the presence of the 11-hydroxy group, the D-homo steroid is treated under heating with aluminum isopropylate in the presence of an aliphatic or cycloaliphatic ketone, such as, for example, acetone or cyclohexanone. However, it is also possible to effect the direct oxidation with oxygen in the presence of platinum dioxide in aqueous acetone.

Suitable solvents are those inert with respect to the oxidizing agents, e.g., aromatic hydrocarbons, such as benzene or toluene, cyclic hydrocarbons, such as hexane, chlorinated hydrocarbons, such as methylene chloride or ethylene chloride, and monocyclic heterocycles, such as pyridine or dioxane.

For the selective reduction of a keto group in the 3- and-or 11-position, the D-homo-20-keto steroid, dissolved in an inert solvent, is hydrogenated either at temperatures below room temperature with a complex metal hydride, such as, for example, lithium aluminum tri-tert.-butoxyhydride or sodium borohydride, or directly with hydrogen in the presence of Raney nickel in a lower carboxylic acid, such as, for example, formic acid or acetic acid under pressure in a range of 30-300 atmospheres gauge. Solvents inert with respect to complex metal hydrides are, for example, ethers, such as diethyl ether or tetrahydrofuran, dioxane, ethylene glycol dimethyl ether, and diethylene glycol dimethyl ether, optionally alcohols, such as methanol or ethanol. However, another suitable method is the reduction with triphenylphosphine in isopropanol in the presence of iridium tetrachloride. An optionally saponification can take place according to conventional methods, for example, with alcoholic potassium hydroxide solution or with methanolic hydrochloric acid.

The optionally subsequent esterification to form the desired final acyloxy group also takes place according to known methods. Preferred is the reaction with a reactive acid derivative in the presence of an alkaline reagent, such as, for example the reaction with an acid chloride or acid anhydride in the presence of pyridine.

A compound produced according to the process of this invention can be converted into another compound of Formula I. This variation of the process can be employed, in particular, for the conversion of the equatorial 3β-alcohols into the corresponding axial 3α-alcohols. A corresponding inversion is also possible with the 16-ols.

Thus, it is possible to produce a 3α-hydroxy-D-homo-5α-pregnan-20-one, via the intermediate stage of the 3β-mesyloxy steroid, which is treated with lithium acetate under heating and then with potassium hydroxide solution, from the corresponding 3β-hydroxy-D-homo-5α-pregnane-20-one.

It is also possible to oxidize the 3β-hydroxy-D-homo-5α-pregnane by chromic acid oxidation to the 3-keto-D-homo-5α-pregnane which is hydrogenated, with Raney nickel, under pressure and in the presence of a lower carboxylic acid to produce the corresponding 3α-hydroxy-D-homo-5α-pregnane.

A preferred embodiment resides in reacting a 3β-hydroxy-D-homo-5α-pregnane with triphenylphosphine and formic acid in the presence of the diethyl ester of azodicarboxylic acid to obtain the 3α-formyloxy-D-homo-5α-pregnane, and then saponifying the latter, for example, with methanolic potassium hydroxide solution to the corresponding 3α-hydroxy-D-homo-5α-pregnane.

The methods described for the 3-ols can also be applied in the same manner to the 16-ols.

The novel steroid compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include, but are not limited to, water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparation can be sterilized and if desired mixed with auxiliary agents, e.g., lubricants, preservatives, stabilizers, wetting agents, emulsifiers, salts for influencing osmotic pressure, buffers, coloring, flavoring and/or aromatic substance and the like which do not deleteriously react with the active compounds.

They can be administered in the same manner as the known alphaxolone.

For parenteral application, particularly suitable are solutions, preferably oily, e.g., sesame oil or castor oil, which can contain additionally a diluent, e.g., benzyl benzoate or benzyl alcohol, or aqueous solutions, as well as suspensions, emulsions or implants. Prefered is a solution in polyhydroxyethoxylated castor oil. Ampoules are convenient unit dosages.

Generally, the compounds of the invention are dispensed in unit dosage form comprising 1-10 ml. of a pharmaceutical carrier per each unit dosage, and the amount per unit dosage is about 5 mg. to 100 mg., preferably about 10 to 40 mg., of active agent of this invention. Preferably, with solutions for parenteral administration, 5 to 20 mg/ml. of solution is employed.

The compounds of this invention are generally administered to animals, including but not limited to mammals, e.g., humans. An anesthetically effective dosage of the active compounds as administered parenterally to humans generally comprises about 0.1-5 mg/kg. of body weight. The compounds are administered preferably intravenously, preferably at a rate of about 1 ml per 10 seconds.

Use for Induction of Anaesthesia

A volunteer male patient of 64 kgs. is given intravenously 0.05 ml/kg, i.e. 3.2 ml. of a solution of 10 mg/ml of 3α-hydroxy-D-homo-5α-pregnan-20-one in an aqueous solution containing 20% of a polyoxyethylated castor oil. This dose produce unconsciousness in half-a-minute. After muscle relaxation with 20 mg. of succinylcholine in a sterile isotonic aqueous solution of 0.9% sodium chloride the patient is intubated and as adequate anaesthesic nitrous oxide/oxygen (65:35) plus 1% of 2-bromo-2-chloro-1,1,1-trifluoro-ethane (halothane Brit. Pharm. 1970) is applied.

Use as Main Anaesthesic

A volunteer male patient of 54 kgs. is given 0.066 ml/kg, i.e. 3.6 ml. of a solution of 5 mg/ml of 3α-hydroxy-D-homo-5α-pregnan-20-one in an aqueous solution containing 20% of a polyoxyethylated castor oil. The solution is administered during 30 seconds. After the patient has become unconscious and minor surgical intervention is performed. After 5 min. a second injection of 1.8 ml of the above-described solution is administered. After 8 min. the patient recovers from anaesthesia.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are indicated in degrees Celsius.

EXAMPLE 1

38.9 g. of 3α-acetoxy-D-homo-5β-pregnane-11,20-dione [produced, for example, according to R. O. Clinton et al., JACS 80, 3395 (1958)] is agitated in 400 ml. of methanol and 400 ml. of methylene chloride with 8 g. of potassium hydroxide for 2 hours at room temperature. After adding 8 ml. of acetic acid, the mixture is evaporated under vacuum. The residue is taken up in methylene chloride, and the methylene chloride solution is washed with water and evaporated under vacuum. The residue is recrystallized from methanol, thus obtaining 32.1 g. of 3α-hydroxy-D-homo-5βpregnane-11,20-dione, m.p. 202°-204°.

EXAMPLE 2

A solution of 4.2 g. of 3β-hydroxy-D-homo-pregna-5,17(17a)-dien-20-one in 500 ml. of methanol is hydrogenated in the presence of 900 mg. of palladium charcoal (10%) until the hydrogen absorption is terminated. The catalyst is filtered off and the solution evaporated under vacuum. After recrystallization from methanol, 3.1 g. of 3β-hydroxy-D-homo-5α-pregnan-20-one is obtained, m.p. 190°-191°.

EXAMPLE 3

30 g. of 3β-hydroxy-D-homo-pregna-5,17(17a)-dien-20-one is heated with 875 ml. of toluene and 250 ml. of cyclohexanone to the boiling point; about 200 ml. is distilled off, and 13.75 g. of aluminum isopropylate, dissolved in 125 ml. of toluene, is added thereto. The reaction mixture is heated for 45 minutes while distilling off part of the mixture to a slight extent, and thereafter the mixture is cooled to 20°, washed with 1N hydrochloric acid and water, and concentrated by evaporation under vacuum. The oily residue crystallizes when combined with pentane. The pentane solution is decanted off and the thus-obtained crude product is recrystallized from acetone-hexane, thus obtaining 20.5 g. of D-homo-pregna-4,17(17a)-diene-3,20-dione, m.p. 169°-171°.

11 g. of D-homo-pregna-4,17(17a)-diene-3,20-dione is dissolved in 300 ml. of ethanol and hydrogenated after adding 1.1 g. of 10% palladium charcoal. The catalyst is filtered off and the solution evaporated. By chromatography on silica gel (gradient: methylene chloride/methylene chloride-ethyl acetate 8:2), 4.2 g. of D-homo-5β-pregnane-3,20-dione (m.p. 164°-165° after recrystallization from methanol) and 2.7 g. of D-homo-5α-pregnane-3,20dione (m.p. 150.5°-151° after recrystallization from acetone-hexane) are obtaind.

EXAMPLE 4

One gram of D-homo-5α-pregnane-3,20-dione is dissolved in 50 ml. of tetrahydrofuran, cooled to −15°, and combined with 1.3 g of lithium aliminum tri-tert.-butoxyhydride. The reaction mixture is agitated for 30 minutes at −15° and then poured into sulfuric ice water. After extraction with methylene chloride and washing with water, the mixture is evaporated under vacuum. Recrystallization from acetone yields 830 mg. of 3β-hydroxy-D-homo-5α-pregnan-20-one, m.p. 190°-191°.

EXAMPLE 5

770 mg. of D-homo-5β-pregnane-3,20-dione is reduced in 40 ml. of tetrahydrofuran with 1 g. of lithium aluminum tri-tert.-butoxyhydride at −15° within 30 minutes. After working up the reaction mixture as described in Example 4, 577 mg. of 3α-hydroxy-D-homo-5β-pregnan-20-one is obtained, m.p. 147°-148°.

EXAMPLE 6

5 g. of 21-acetoxy-3β-hydroxy-D-homo-5-pregnen-20-one [produced, for example, according to R. M. Dodson et al., JACS 75, 5132 (1953)] is hydrogenated in 500 ml. of methanol after adding 500 mg. of 10% palladium charcoal. The catalyst is filtered off and the solution concentrated until the onset of crystallization, thus obtaining 4.6 g. of 21-acetoxy-3β-hydroxy-D-homo-5α-pregnan-20-one, m.p. 159°-160°.

EXAMPLE 7

A solution of 2.3 g. of 3β-hydroxy-D-homo-5α-pregnan-20-one in 20 ml. of pyridine is cooled to 0° and combined dropwise under stirring with 1.15 ml. of methanesulfochloride. The mixture is agitated for 30 minutes at 20°, then precipitated into ice water, and the thus-precipitated product is vacuum filtered, taken up in methylene chloride, washed with water, and evaporated under vacuum. An analytical sample of the 3β-mesyloxy-D-homo-5α-pregnan-20-one melts, after recrystallization from acetone, at 139°-140°.

EXAMPLE 8

2.8 g. of the crude mesylate is refluxed for 3 hours in 100 ml. of glacial acetic acid with 5 g. of lithium acetate. Thereafter, the solution is evapoated under vacuum, the residue dissolved in methylene chloride, washed with a sodium bicarbonate solution and water, and evaporated, thus obtaining 2.6 g of 3α-acetoxy-D-homo-5α-pregnan-20-one, m.p.152°-153.5°.

EXAMPLE 9

2.6 g. of 3α-acetoxy-D-homo-5α-pregnan-20-one is refluxed in 150 ml. of methanol and 300 mg. of potassium hydroxide for 5 hours. After adding 1 ml. of glacial acetic acid, the mixture is evaporated under vacuum, taken up in methylene chloride, washed with water, and concentrated to dryness. By layer chromatography in the system methylene chloride-ethyl acetate 95:5, 950 mg. of 3α-hydroxy-D-homo-5α-pregnan-20-one is separated and recrystallized from acetone, m.p. 161°-162°.

EXAMPLE 10

1.9 g. of 21-acetoxy-D-homo-4-pregnene-3,20-dione [produced, for example, according to Dodson, JACS 75, 5132 (1953)] is hydrogenated in 400 ml. of dimethylformamide after adding 190 mg. of 10% palladium charcoal. The catalyst is filtered off, the filtrate is evaporated under vacuum, and the residue is separated by layer chromatography in the system ether-pentane 1:1. After recrystallization from acetone-hexane, 523 mg. of 21-acetoxy-D-homo-5α-pregnane-3,20-dione, m.p. 168°-169°, and 806 mg. of 21-acetoxy-D-homo-5β-pregnane-3,20-dione, m.p. 127°-128°, are produced.

EXAMPLE 11

A 2-liter Erlenmeyer flask, containing 500 ml. of a nutrient solution sterilized for 30 minutes at 120° in an autoclave, made up from 1% corn steep liquor, 1% soybean meal, and 0.005% soybean oil, adjusted to pH 6.2, is inoculated with a lyophilized culture of *Curvularia lunata* and shaken for 72 hours at 30° on a rotary shaker. By means of this subculture, a 20-liter fermentor is inoculated, this fermentor consisting of stainless steel and containing 15 l. of a medium sterilized at 121° and under 1.1 atmospheres gauge made up of 1% corn steep liquor, 0.5% glucose, and 0.005% soybean oil, adjusted to pH 6.2. With the addition of "Silicone SH" as a defrother, the mixture is incubated for 24 hours at 29° under aeration (10 l./minute) and under a pressure of 0.7 atmosphere gauge and while agitating the mixture (220 r.p.m.). One liter of the culture broth is transferred under sterile conditions into 14 l. of a medium, sterilized as above, consisting of 1% corn steep liquor, 1.25% soybean meal, and 0.005% soybean oil, and grown under the same conditions. After 6 hours, a solution of 3 g. of 21-acetoxy-D-homo-4-pregnene-3,20-dione in 150 ml. of dimethylformamide is added thereto.

The course of the conversion is observed by analyzing the fermentor samples, extracted with methyl isobutyl ketone, by means of thin-layer chromatography. After a complete conversion has been achieved (23 hours of contact time), the content of the fermentor is extracted twice with respectively 10 l. of methyl isobutyl ketone, and the extract is evaporated under vacuum at a bath temperature of 50°. The residue is purified by chromatography on silica gel and recrystallized from acetone-ether, thus obtaining 11β,21-dihydroxy-D-homo-4-pregnene-3,20dione, m.p. 191°-195°.

5.6 g. of 11β,21-dihydroxy-D-homo-4-pregnene-3,20-dione is mixed wih 50 ml. of dimethylformamide, 10 ml. of acetic anhydride, and 5.5 g. of lead diacetate and agitated for 1.5 hours at 20°. Then, the mixture is poured into ice-cold sodium chloride solution; the precipitated product is filtered and taken up in methylene chloride. The solution is washed with water, evaporated under vacuum, and the residue is recrystallized from acetone-hexane, thus obtaining 5.2 g. of 21-acetoxy-11β-hydroxy-D-homo-4-pregnene-3,20-dione.

3.3 g. of 21-acetoxy-11β-hydroxy-D-homo-4-pregnene-3,20-dione is hydrogenated as described in Example 10. The separation of the epimers on the $C_5$ carbon atom is accomplished by layer chromatography in the system methylene chloride/ethyl acetate 9:1. After recrystallization from acetone-hexane, 1.2 g. of 21-acetoxy-11β-hydroxy-D-homo-5α-pregnane-3,20-dione, m.p. 171°–173°, and 925 mg. of 21-acetoxy-11β-hydroxy-D-homo-5β-pregnane-3,20-dione, m.p. 136°–138°, are obtained.

EXAMPLE 12

900 mg. of 21-acetoxy-11β-hydroxy-D-homo-5α-pregnane-3,20-dione is dissolved in 15 ml. of methylene chloride; then, 60 ml. of a chromic acid solution (produced from 6 g. of $CrO_3$, 150 ml. of methylene chloride, and 9.5 ml. of pyridine) is added thereto and the mixture agitated for 10 minutes at room temperature. Thereafter, 3 ml. of methanol is added, and the mixture is diluted with methylene chloride, filtered over silica gel, the filtrate washed with water, and concentrated. After recrystallization from acetone-hexane, 755 mg. of 21-acetoxy-D-homo-5α-pregnane-3,11,20-trione is produced, m.p. 187°–188.5°.

EXAMPLE 13

One gram of 21-acetoxy-D-homo-5α-pregnane-3,11,20-trione is dissolved in 50 ml. of glacial acetic acid, charged into a 150-ml. tumbling autoclave and hydrogenated, after the addition of 2 g. of freshly prepared Raney nickel, at a hydrogen pressure of 132 atmospheres gauge. The hydrogen absorption is terminated after 30 minutes. The catalyst is filtered off, washed with glacial acetic acid, and the filtrate concentrated under vacuum to one-third its volume, and then poured into ice water under stirring. The thus-precipitated product is vacuum-filtered, washed with water, dried, and recrystallized in acetone-hexane, thus obtaining 720 mg. of 21-acetoxy-3α-hydroxy-D-homo-5α-pregnane-11,20-dione, m.p. 195°–197°. By means of layer chromatography of the mother liquor, 110 mg. of 21-acetoxy-3β-hydroxy-D-homo5α-pregnane-11,20-dione can be obtained, melting at 173°–175° after recrystallization from acetone-hexane.

EXAMPLE 14

10 g. of 3β-hydroxy-D-homo-pregna-5,17(17a)-dien-20-one is dissolved in 1,000 ml. of glacial acetic acid and hydrogenated, after the addition of 1 g. of platinum dioxide, until the hydrogen absorption has ceased. The catalyst is filtered off, the filtrate is cooled to 10° and, under agitation, a solution of 25 g. of chromium trioxide in 100 ml. of water is added dropwise thereto. The mixture is then poured into ice water, the precipitated product is vacuum filtered, washed with water, and dried. After recrystallization from acetone-hexane, 8.5 g. of D-homo-5α-pregnane-3,20-dione is obtained, m.p. 150.5°–151.5°.

EXAMPLE 15

A 2-liter Erlenmeyer flask, containing 500 ml. of a nutrient solution, sterilized for 30 minutes at 120° in an autoclave, made up of 1% corn steep liquor, 1.25% soybean meal, and 0.005% soybean oil, adjusted to pH 6.2, is inoculated with a lyophilized culture of *Aspergillus ochraceus* (ATCC 1008) and shaken on a rotary vibrator for 72 hours at 30°.

With this subculture, ten 2-liter Erlenmeyer flasks are then inoculated, which flasks had been filled with respectively 500 ml. of sterilized nutrient medium of 1% corn steep liquor, 1.25% soybean meal, and 0.005% soybean oil. After 6 hours of shaking on a rotary vibrator, each flask receives, under sterile conditions, 100 mg. of D-homo-progesterone [prepared, for example, according to Dodson, JACS 75, 5132 (1953)], dissolved in 5 ml. of dimethylformamide. Thereafter, the mixture is incubated for another 48 hours on the vibrator.

The contents of all flasks are subsequently combined and exhaustively extracted with methyl isobutyl ketone. The combined organic extracts are evaporated under vacuum, the oily residue is made to crystallize by digestion with ethyl acetate/ether and finally recrystallized from ethyl acetate, thus obtaining 11α-hydroxy-D-homo-4-pregnene-3,20-dione, m.p. 196°–197°. $R_f = 0.65$ in the system chloroform-methanol 9 + 1.

Under the above-described conditions, 1 g. of D-homo-progesterone, distributed over ten large shake flasks, is fermented for 30 hours with the microorganism strain *Curvularia lunata* (NRRL 2178) and worked up as described above. The thus-obtained 11β-hydroxy-D-homo-4-pregnene-3,20-dione shows in thin-layer chromatography an $R_f$ value of 0.71 (silica gel plates, Merck, system chloroform-methanol 9 + 1).

11α- and/or 11β-hydroxy-D-homo-4-pregnene-3,20-dione is oxidized respectively as described in Example 12, and the thus-produced D-homo-4-pregnene-3,11,20-trione is recrystallized from acetone-hexane, m.p. 168°–169.5°.

30.5 g. of D-homo-4-pregnene-3,11,20-trione is hydrogenated in 1,000 ml. of dimethylformamide in the presence of 3 g. of 10% palladium charcoal. After the reaction mixture has been worked up and chromatographed as set forth in Example 3, recrystallization from acetone-hexane yields 12.3 g. of D-homo-5β-pregnane-3,11,20-trione (m.p. 146°–147.5°) and 14.1 g. of D-homo-5α-pregnane-3,11,20-trione (m.p. 132°–134°)

EXAMPLE 16

Analogously to Example 4, by reduction with lithium aluminum tri-tert.-butoxyhydride, 3α-hydroxy-D-homo-5β-pregnane-11,20-dione is obtained from D-homo-5β-pregnane-3,11,20-trione and correspondingly 3β-hydroxy-D-homo-5α-pregnane-11,20-dione is produced from D-homo-5α-pregnane-3,11,20-trione.

EXAMPLE 17

According to the process set forth in Examples 7–9, 3α-hydroxy-D-homo-5α-pregnane-11,20-dione is obtained from 3β-hydroxy-D-homo-5α-pregnane-11,20-dione; this final product melts at 175°–176° after recrystallization from acetone-hexane.

EXAMPLE 18 b 2.1 g. of 21-acetoxy-D-homo-5α-pregnane-3,20-dione is stirred in 250 ml. of methylene chloride and 250 ml. of 1% methanolic potassium hydroxide solution for 2 hours at 20°. After neutralization with acetic acid, the mixture is concentrated by evaporation under vacuum, taken up in tetrahydrofuran, filtered off from the potassium acetate, and concentrated under vacuum. The thus-obtained crude 21-hydroxy-D-homo-5α-pregnane-3,20-dione is heated in 60 ml. of pyridine with 6 ml. of butyric acid anhydride for 15 minutes to the boiling point. After cooling, the mixture is diluted with cyclohexane and evaporated under vacuum. This procedure is repeated three times. The oily residue is triturated with pentane, the pentane solution is decanted off, and the crude product is recrystallized from acetone-hexane, thus obtaining 1.3 g. of 21-butyryloxy-D-homo-5α-pregnane-3,20-dione, m.p. 112°–114°.

EXAMPLE 19

5 g. of 3β-hydroxy-D-homo-5α-pregnan-20-one is dissolved in 90 ml. of tetrahydrofuran; 8.3 g. of triphenylphosphine and 1.125 ml. of formic acid are added thereto and, under stirring, a solution of 4.75 ml. of the diethyl ester of azodicarboxylic acid in 10 ml. of tetrahydrofuran is then gradually added dropwise to the reaction mixture. The reaction solution is stirred for 1 hour and poured into ice water. The thus-precipitated product is vacuum filtered, taken up in methylene chloride, washed with water, and evaporated under vacuum. The residue is purified by chromatography on silica gel, and the thus-produced 3α-formyloxy-D-homo-5α-pregnan-20-one is recrystallized from acetone-hexane; yield: 85%; m.p. 158.5°–159.5°.

EXAMPLE 20

100 mg. of 3α-formyloxy-D-homo-5α-pregnan-20-one is dissolved in 1 ml. of methylene chloride and 1 ml. of methanol and, after adding 22 mg. of potassium hydroxide, agitated for 20 minutes at room temperature. After neutralization with acetic acid, the mixture is evaporated under vacuum, the residue dissolved in methylene chloride, washed with water, and evaporated. After recrystallization from acetone, 68 mg. of 3α-hydroxy-D-homo-5α-pregnan-20-one is obtained, m.p. 161.5°–162.5°.

EXAMPLE 21

Analogously to Example 19, 21-acetoxy-3α-formyloxy-D-homo-5α-pregnan-20-one, m.p. 187.5°–188°, is produced from 21-acetoxy-3β-hydroxy-D-homo-5α-pregnan-20-one.

EXAMPLE 22

880 mg. of 21-acetoxy-3α-formyloxy-D-homo-5α-pregnan-20-one is dissolved in 20 ml. of methylene chloride and 20 ml. of methanol, combined with 400 mg. of potassium hydroxide, and agitated for 90 minutes at 20°. After neutralization with acetic acid, the mixture is evaporated under vacuum. The thus-produced crude 3α,21-dihydroxy-D-homo-5α-pregnan-20-one is stirred for 1.5 hours at 20° with 6 ml. of dimethylformamide, 1.2 ml. of acetic anhydride, and 84 mg. of lead diacetate. Thereafter, the mixture is precipitated into ice water, the reaction product is vacuum filtered, washed with water, dried, and recrystallized from acetone-hexane, thus obtaining 589 mg. of 21-acetoxy-3α-hydroxy-D-homo-5α-pregnan-20-one, m.p. 173.5°–174°.

EXAMPLE 23

240 mg. of 3β-hydroxy-D-homo-5α-pregnane-11,20-dione is dissolved in 5 ml. of absolute tetrahydrofuran; 400 mg. of triphenylphosphine and 0.053 ml. of formic acid are added to the reaction mixture, and then 0.235 ml. of the ethyl ester of azodicarboxylic acid is added dropwise thereto. The mixture is agitated for 30 minutes at 20° and then worked up as set forth in Example 19. By layer chromatography in the system methylene chloride-ethyl acetate and by recrystallization from isopropyl ether, 204 mg. of 3α-formyloxy-D-homo-5α-pregnane-11,20-dione is obtained, m.p. 171°–173°.

EXAMPLE 24

3α-Formyloxy-D-homo-5α-pregnane-11,20-dione is saponified and worked up as set forth in Example 20. After recrystallizing twice from methylene chloride-isopropyl ether, 3α-hydroxy-D-homo-5α-pregnane-11,20-dione is obtained, m.p. 196°–197° (yield: 95% of theory).

EXAMPLE 25

Analogously to Example 13, D-homo-5β-pregnane-3,20-dione is hydrogenated to 3β-hydroxy-D-homo-5β-pregnan-20-one. This product, after being recrystallized twice from isopropyl ether, melts at 187°–188° (yield: 81% of theory).

EXAMPLE 26

20 g. of 3β-acetoxy-17α-methyl-D-homo-5-pregnen-20-one is hydrogenated in 1,000 ml. of ethyl acetate with hydrogen, after adding 4 g. of 10% palladium charcoal. Thereafter, the catalyst is filtered off, the filtrate is evaporated, and the residue is recrystallized from hexane, thus obtaining 17.5 g. of 3β-acetoxy-17α-methyl-D-homo-5α-pregnan-20-one, m.p. 178.5°–179°.

The starting material, 3β-acetoxy-17α-methyl-D-homo-5-pregnen-20-one is produced as follows:

130 ml. of methyl iodide is added dropwise to 45 g. of magnesium filings in 1,400 ml. of absolute ether. After the magnesium has been dissolved, 2,500 ml. of absolute tetrahydrofuran is gradually added to the reaction mixture, and the latter is distilled until the distillate has reached a boiling point of 55°. The mixture is then cooled to −20° and combined with 7 g. of copper (I) chloride and with a solution of 100 g. of 3β-acetoxy-D-homo-5,17(17a)-dien-20-one in 1,000 ml. of absolute tetrahydrofuran, whereupon the mixture is stirred for 40 minutes at 20°. Then, the mixture is cooled to 0°, and 230 ml. of 2N sulfuric acid is introduced dropwise into the mixture; then an extraction with ethyl acetate is carried out. The extract is washed with sodium thiosulfate solution and water, dried over sodium sulfate, and concentrated under vacuum.

The thus-obtained residue is mixed under heating with 300 ml. of pyridine and 150 ml. of acetic anhydride, and the thus-produced solution is allowed to stand for 16 hours at room temperature. Thereafter, the mixture is poured into ice water; the precipitated product is vacuum filtered and dissolved in methylene chloride. The methylene chloride solution is washed with dilute sulfuric acid and water, concentrated under vacuum, and the residue recrystallized from methylene chloride-ethyl acetate, thus obtaining 75.6 g. of 3β-acetoxy-17α-methyl-D-homo-5-pregnen-20-one, m.p. 212°–213°.

EXAMPLE 27

21 g. of 3β-acetoxy-17α-methyl-D-homo-5α-pregnan-20-one is dissolved in 200 ml. of methylene chloride and 200 ml. of methanol, combined with 4 g. of potassium hydroxide, and agitated for 4 hours at 20°. After the addition of 5 ml. of glacial acetic acid, the mixture is evaporated under vacuum, the residue taken up in chloroform, washed with water, and dried. The chloroform solution is concentrated and the remaining residue is recrystallized from acetone, yielding 15.1 g. of 3β- hydroxy-17α-methyl-D-homo-5α-pregnan-20-one, m.p. 217°–218°.

EXAMPLE 28

A solution of 2.0 g. of 3β-hydroxy-17α-methyl-D-homo-5α-pregnan-20-one in 20 ml. of pyridine is cooled to 0° and combined dropwise under agitation with 1.15 ml. of methane-sulfochloride. The mixture is stirred for another 30 minutes at 20°, precipitated into ice water, the precipitated product vacuum filtered, taken up in methylene chloride, washed with water, and evaporated under vacuum.

2.6 g. of the crude mesylate is heated under reflux for 3 hours in 100 ml. of glacial acid with 5 g. of lithium acetate. Thereafter, the solution is evaporated under vacuum, the residue is dissolved in methylene chloride, washed with a sodium bicarbonate solution and water, and evaporated, yielding 2.3 g. of 3α-acetoxy-17α-methyl-D-homo-5α-pregnan-20-one.

2.3 g. of 3α-acetoxy-17α-methyl-D-homo-5α-pregnan-20-one is refluxed in 150 ml. of methanol and 300 mg. of potassium hydroxide for 5 hours. After adding 1 ml. of glacial acetic acid, the mixture is evaporated under vacuum, taken up in methylene chloride, washed with water, and evaporated to dryness. By layer chromatography in the system methylene chloride-ethyl acetate 95:5, 950 mg. of 3α-hydroxy-17α-methyl-D-homo-5α-pregnan-20-one is separated and recrystallized from acetone, m.p. 161°–162°.

EXAMPLE 29

5 g. of 3β,16α-dihydroxy-D-homo-5-pregnen-20-one (produced, for example, according to U.S. Pat. No. 2,822,381) is dissolved in 400 ml. of ethanol; then, 1 g. of 10% palladium charcoal is added thereto and the reaction mixture is hydrogenated with hydrogen. Subsequently, the catalyst is filtered off, the filtrate is evaporated under vacuum, and the residue is recrystallized from ethyl acetate, thus obtaining 3.92 g. of 3β,16α-dihydroxy-D-homo-5α-pregnan-20-one, m.p. 215°–216°.

EXAMPLE 30

1.65 g. of 3β,16α-dihydroxy-D-homo-5α-pregnan-20-one is dissolved in 30 ml. of tetrahydrofuran, combined with 5.21 g. of triphenylphosphine and 0.71 ml. of formic acid, and 3.08 ml. of the diethyl ester of azodicarboxylic acid in 12 ml. of tetrahydrofuran is added dropwise. The mixture is stirred at 20° for 30 minutes and then poured into ice water. The thus-precipitated product is vacuum filtered, taken up in methylene chloride, washed with water, and evaporated.

The remaining residue is purified by chromatography on silica gel. By elution with hexane-ethyl acetate 8:2, 1.24 g. of 3α,16β-diformyloxy-D-homo-5α-pregnan-20-one is obtained.

EXAMPLE 31

1.04 g. of 3α,16β1-diformyloxy-D-homo-5α-pregnan-20-one is dissolved in 10 ml. of methylene chloride and 10 ml. of methanol and, after the addition of 400 mg. of potassium hydroxide, agitated for 30 minutes at room temperature. After working up the reaction mixture as described in Example 20 and recrystallization from ethyl acetate, 0.82 g. of 3α,16β-dihydroxy-D-homo-5α-pregnan-20-one is obtained, m.p. 237.5°–238°.

EXAMPLE 32

100 g. of 3β-acetoxy-D-homo-pregna-5,17-dien-20-one is dissolved in 500 ml. of tetrahydrofuran and 500 ml. of dimethylformamide; 5 g. of 5% palladium charcoal is added thereto and the mixture is hydrogenated. The catalyst is vacuum filtered, washed with methylene chloride, and the filtrate concentrated under vacuum for crystallization purposes.

The thus-crystallized 3β-acetoxy-D-homo-5-pregnen-20-one (m.p. 183°–185°; 80 g.) is vacuum filtered. The mother liquors are evaporated and chromatographed on silica gel. With hexane-isopropyl ether (7:3), 11.8 g. of 3β-acetoxy-D-homo-17aα-pregn-5-en-20-one is eluted and recrystallized from ethyl acetate, m.p. 191°–192.5°.

EXAMPLE 33

1.88 g. of 3β-acetoxy-D-homo-17aα-pregn-5-en-20-one is dissolved in 10 ml. of methylene chloride and 10 ml. of methanol. After adding 320 mg. of potassium hydroxide, the mixture is agitated for 1 hour at room temperature. The mixture is then neutralized with acetic acid, evaporated under vacuum, taken up in tetrahydrofuran, filtered off from the potassium acetate, concentrated under vacuum, and recrystallized from ethyl acetate, thus producing 1.27 g. of 3β-hydroxy-D-homo-17aα-pregn-5-en-20-one, m.p. 173°–174°.

EXAMPLE 34

900 mg. of 3β-hydroxy-D-homo-17aα-pregn-5-en-20-one is hydrogenated in 60 ml. of ethanol after adding 180 mg. of 10% palladium charcoal. The catalyst is then filtered off, the filtrate is evaporated, and the residue is recrystallized from ethyl acetate, yielding 680 mg. of 3β-hydroxy-D-homo-5 α,17a α-pregnan-20-one, m.p. 168°–169°.

EXAMPLE 35

500 mg. of 3β-hydroxy-D-homo-5α,17a-pregnan-20-one is reacted analogously to Examples 19 and 20. After recrystallization from acetone-hexane, 307 mg. of 3α-hydroxy-D-homo-5α,17aα-pregnan-20-one is obtained, m.p. 194°–195°.

EXAMPLE 36 a. 5 g. of 3β,20-diacetoxy-D-homo-pregna-5,16,17a(20)-triene (produced as described, for example, in German Pat. No. 1,135,903) is agitated in 500 ml. of acetic anhydride with 3 ml. of boron trifluoride etherate for 5 minutes at 20°. The mixture is then stirred into ice water and extracted with methylene chloride. The methylene chloride solution is washed with water and concentrated under vacuum. The residue is dissolved in 50 ml. of isopropanol, combined with 4 ml. of concentrated hydrochloric acid, and heated under reflux for 3 hours. After cooling, the mixture is diluted with methylene chloride, washed with water, and evaporated to dryness. By chromatography on silica gel with methylene chloride-acetone 7:3, 2.1 g. of 16-acetyl-3β-hydroxy-D-homo-pregna-5,16-dien-20-one is eluted, m.p. 203°–208° (methylene chloride-methanol).

b. 5.55 g. of 16-acetyl-3β-hydroxy-D-homo-pregnan-5,16-dien-20-one is dissolved in 150 ml. of tetrahydrofuran and 260 ml. of ethanol; then, 500 mg. of 5% palladium charcoal is added thereto and the mixture hydrogenated. Thereafter, the catalyst is filtered off and the filtrate evaporated under vacuum. The residue is chromatographed on silica gel. By elution with hexane-acetone 7:3, one obtains 1.93 g. of 16β-actyl-3β-hydroxy-D-homo-5α-pregnan-20-one; this product is recrystallized from actone-hexane, m.p. 181°–182°.

EXAMPLE 37

374 mg. of 16β-acetyl-3β-hydroxy-D-homo-5α-pregnan-20-one is dissolved in 10 ml. of tetrahydrofuran; 524 mg. of triphenylphosphine and 92 mg. of formic acid are added, and the mixture is combined with 349 mg. of the ethyl ester of azodicarboxylic acid in 4 ml. of tetrahydrofuran by adding the ester dropwise to the mixture. The latter is agitated for 1 hour at 20° and then worked up as described in Example 19. The residue is chromatographed on silica gel. With hexaneacetone 9:1, 320 mg. of 16β-acetyl- 3α-formyloxy-D-homo-5α-pregnan-20-one is eluted and recrystallized from acetonehexane, m.p. 148°–148.5°.

EXAMPLE 38

276 mg. of 16β-acetyl-3α-formyloxy-D-homo-5α-pregnan-20-one is dissolved in 5 ml. of methanol and 3 ml. of methylene chloride and then, after the addition of 60 mg. of potassium hydroxide, agitated for 1 hour at 20°. After working up the mixture as described in Example 20 and recrystallization from actone-hexane, 169 mg. of 16β-acetyl-3α-acetyl-3α-hydroxy-D-homo-5α-pregnan-20-one is obtained, m.p. 162.5°–163°.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A D-homo-20-ketopregnane of the formula

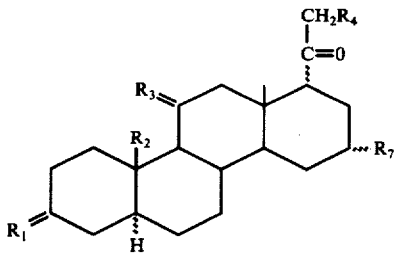

wherein $R_1$ is an oxygen atom

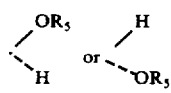

in which $R_5$ is hydrogen or the acyl radical of a hydrocarbon carboxylic or sulfonic acid of up to 8 carbon atoms; $R_2$ is hydrogen or methyl; $R_3$ is an oxygen atom,

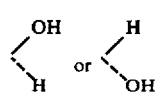

or two hydrogen atoms; $R_4$ is hydrogen, hydroxy, or hydrocarbon acyloxy of up to 15 carbon atoms; and $R_7$ is hydroxy or lower-alkanoyloxy.

2. A compound of claim 1, wherein $R_2$ is $CH_3$, the side chain at the $C_{17a}$ carbon atom is in the beta position, and the 5-position hydrogen atom is in the alpha position.

3. 3α-Hydroxy-D-homo-5α-pregnan-20-one.

4. 3α-Hydroxy-D-homo-5α-pregnane-11,20-dione.

5. A method of inducing general anesthesia in a mammal which comprises administering thereto an amount effective to induce general anesthesia of a compound of the formula

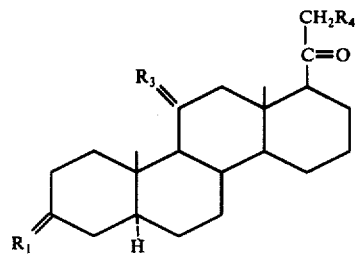

wherein $R_1$ is an oxygen atom

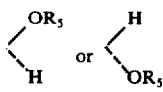

in which $R_5$ is hydrogen or the acyl radical of a hydrocarbon carboxylic or sulfonic acid of up to 8 carbon atoms; $R_3$ is an oxygen atom

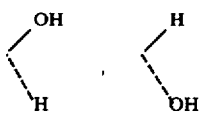

or two hydrogen atoms; and $R_4$ is hydrogen, hydroxy or hydrocarbon acyloxy of up to 15 carbon atoms.

6. A method of claim 5, said compound being 3-β-hydroxy-D-homo-5α-pregnan-20-one.

7. A method of claim 5, said compound being 21-acetoxy-3β-hydroxy-D-homo-5α-pregnan-20-one.

8. A method of claim 5, said compound being 3β-mesyloxy-D-homo-5α-pregnan-20-one.

9. A method of claim 5, said compound being 3α-acetoxy-D-homo-5α-pregnan-20-one.

10. A method of claim 5, said compound being 21-acetoxy-3α-hydroxy-D-homo-5α-pregnane-11,20-dione.

11. A method of claim 5, said compound being 21-acetoxy-3β-hydroxy-D-homo-5α-pregnane-11,20-dione.

12. A method of claim 5, said compound being 3β-hydroxy-D-homo-5α-pregnane-11,20-dione.

13. A method of claim 5, said compound being 3α-formyloxy-D-homo-5α-pregnan-20-one.

14. A method of claim 5, said compound being 21-acetoxy-3α-formyloxy-D-homo-5α-pregnane-20-one.

15. A method of claim 5, said compound being 3α,21-dihydroxy-D-homo-5α-pregnan-20-one.

16. A method of claim 5, said compound being 21-acetoxy-3α-hydroxy-D-homo-5α-pregnan-20-one.

17. A method of claim 5, said compound being 3α-formyloxy-D-homo-5α-pregnane-11,20-dione.

18. A method of claim 5, said compound being 3α-hydroxy-D-homo-5α-pregnane-11,20-dione.

19. A method of claim 5 wherein R' is an oxygen atom.

20. A method of claim 5 wherein R' is two hydrogen atoms.

21. A method of claim 5 wherein R'' is H.

22. A method of claim 5 wherein R'' is hydroxy.

23. A method of claim 5 wherein R'' is lower alkanoyloxy.

* * * * *